US009714943B2

(12) United States Patent
Stroot et al.

(10) Patent No.: US 9,714,943 B2
(45) Date of Patent: Jul. 25, 2017

(54) METHODS AND MATERIALS FOR CAPTURE ANTIBODY TARGETED FLUORESCENT IN-SITU HYBRIDIZATION (CAT-FISH)

(75) Inventors: Joyce Marie Stroot, Parker, CO (US); Peter George Stroot, Parker, CO (US); Kelly M. Leach, Tampa, FL (US); Daniel Van Lim, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 13/336,800

(22) Filed: Dec. 23, 2011

(65) Prior Publication Data
US 2012/0172245 A1    Jul. 5, 2012

Related U.S. Application Data (60) Provisional application No. 61/465,227, filed on Mar. 16, 2011, provisional application No. 61/428,468, filed on Dec. 30, 2010.

(51) Int. Cl.
C12Q 1/68       (2006.01)
G01N 33/569    (2006.01)

(52) U.S. Cl.
CPC .............................. *G01N 33/56911* (2013.01)

(58) Field of Classification Search
CPC ................... G01N 33/54326; G01N 33/56911
See application file for complete search history.

(56) References Cited

U.S. PATENT DOCUMENTS

| 5,429,797 | A | 7/1995 | Camiener | |
|---|---|---|---|---|
| 5,439,667 | A | 8/1995 | Camiener | |
| 6,007,994 | A * | 12/1999 | Ward | C07H 21/00 435/6.11 |
| 6,861,236 | B2 * | 3/2005 | Moll et al. | 435/69.1 |
| 7,005,257 | B1 * | 2/2006 | Haas et al. | 435/6.12 |
| 7,771,941 | B2 | 8/2010 | Stroot et al. | |
| 2003/0148379 | A1 * | 8/2003 | Roitman et al. | 435/7.1 |
| 2005/0118602 | A1 * | 6/2005 | Li et al. | 435/6 |
| 2007/0128646 | A1 * | 6/2007 | Fiandaca et al. | 435/6 |
| 2008/0113358 | A1 * | 5/2008 | Kapur et al. | 435/6 |
| 2010/0173295 | A1 * | 7/2010 | Lenz | G01N 1/30 435/6.11 |

FOREIGN PATENT DOCUMENTS

| NL | WO 2006018311 A2 * | 2/2006 | ............ B01L 3/5085 |
|---|---|---|---|
| WO | WO 2009085574 A2 * | 7/2009 | ............... G01N 1/44 |

OTHER PUBLICATIONS

Shibutani, M. et al 2002 Methods Enzymol 356: pp. 114-125.*
Kuroda et al 2001 Lancet 357: 1225-1240.*
*Staphylococcus aureus* subsp. *aureus* N315 strain N315 16S ribo-somal RNA, complete sequence. Datasheet [online]. National Center for Biotechnology Information, Jan. 31, 2013 [retrieved on Jul. 13, 2014]. Retrieved from the Internet: <http://www.ncbi.nlm.nih.gov/nuccore/NR_075000>.*
Ramage et al. (Combined fluorescent in situ hybridisation and immunolabelling of Bacteroides fragilis, J Immunol Methods. Mar. 15, 1998;212(2):139-47).*
Oerther et al. (Simultaneous oligonucleotide probe hybridization and immunostaining for in situ detection of *Gordona* species in activated sludge, FEMS Microbiology Ecology, vol. 29, Issue 2, Jun. 1999, pp. 129-136).*
Kemp et al. (Rapid detection and identification of pathogens in blood cultures by fluorescence in situ hybridization and flow cytometry, Int J Med Microbiol. Apr. 2005;295(1):47-55).*
Cox et al. (Assessment of fixatives, fixation, and tissue processing on morphology and RNA integrity, Exp Mol Pathol. Apr. 2006;80(2):183-91. Epub Dec. 5, 2005).*
Kim et al. (Multiplexed magnetic microsphere immunoassays for detection of pathogens in foods, Sens Instrum Food Qual Saf. May 4, 2010; 4(2): 73-81).*
Peters et al. (Rapid Identification of Pathogens in Blood Cultures with a Modified Fluorescence In Situ Hybridization Assay, J Clin Microbiol. Nov. 2006; 44(11): 4186-4188).*
Trebesius et al. (Culture independent and rapid identi®cation of bacterial pathogens in necrotising fasciitis and streptococcal toxic shock syndrome by fluorescence in situ hybridization, Med Microbiol Immunol. Jun. 2000;188(4):169-75).*
Takagi et al. (Microdissected Region-specific Gene Expression Analysis with Methacarn-fixed, Paraffin-embedded Tissues by Real-time RT-PCR, J Histochem Cytochem. Jul. 2004;52(7):903-13).*
Lee et al. (Methacarn fixation—effects of tissue processing and storage conditions on detection of mRNAs and proteins in paraffin-embedded tissues, Anal Biochem. Apr. 1, 2006;351(1):36-43. Epub Feb. 8, 2006).*
Vignali et al. (Multiplexed particle-based flow cytometric assays, J Immunol Methods. Sep. 21, 2000;243(1-2):243-55).*
Kim et al. (Multiplexed Detection of Bacteria and Toxins Using a Microflow Cytometer, Anal. Chem., 2009, 81 (13), pp. 5426-5432, Publication Date (Web): Jun. 4, 2009).*
Nava et al. (Spatial organization of intestinal microbiota in the mouse ascending colon, The ISME Journal (2011) 5, 627-638; published online Oct. 28, 2010).*
Amann, R., et al., "The Identification of Microorganisms by Fluorescence in situ Hybridisation," *Current Opinion in Biotechnology*, 2001, vol. 12, 231-236.
Amann, R., et al., "Fluorescent-Oligonucleotide Probing of Whole Cells for Determinative, Phylogenetic, and Environmental Studies in Microbiology," *Journal of Bacteriology*, 1990, vol. 172, No. 2, pp. 762-770.
Amann, R. I. "Fluorescently Labeled, rRNA-Targeted Oligonucleotide Probes in the Study of Microbial Ecology," *Mol. Ecol.*, 1995, vol. 4, pp. 543-554.

(Continued)

*Primary Examiner* — Aaron Priest
(74) *Attorney, Agent, or Firm* — Saliwanchik, Lloyd & Eisenschenk (57) ABSTRACT

The subject invention concerns materials and methods for detecting a target cell in a population. Methods of the invention comprise internally labeling cells via fluorescence in situ hybridization (FISH) using probes that target rRNA, followed by binding of capture antibodies targeted (CAT) for specific cell surface epitopes on the target cells. In one embodiment, the target cells are bacterial cells.

26 Claims, 4 Drawing Sheets
(1 of 4 Drawing Sheet(s) Filed in Color)

(56) References Cited

OTHER PUBLICATIONS

Amann, R. I., et al., "Combination of 16s rRNA-Targeted Oligonucleotide Probes with Flow Cytometry for Analyzing Mixed Microbial Populations," *Applied and Environmental Microbiology*, 1990, vol. 56, No. 6, pp. 1919-1925.

Aβmus, B., et al., "Improved in situ Tracking of Rhizosphere Bacteria using Dual Staining with Fluorescence-Labeled Antibodies and rRNA-Targeted Oligonucleotides," *Microb Ecol*, 1997, vol. 33, pp. 32-40.

Baumgärtner, W., et al. "Evaluation of Different Fixatives and Treatments for Immunohistochemical Demonstration of *Coxiella burnetii* in Paraffin-Embedded Tissues," *Journal of Clinical Microbiology*, 1988, vol. 26, No. 10, pp. 2044-2047.

Bisha, B. And Brehm-Stecher, B. F., "Flow-Through Imaging Cytometry for Characterization of *Salmonella* Subpopulations in Alfalfa Sprouts, a Complex Food System," *Biotechnol. J.*, 2009, vol. 4, pp. 880-887.

Bisha, B. and Brehm-Stecher, B. F., "Simple Adhesive-Tape Sampling of Tomato Surfaces Combined with Rapid Fluorescence In Situ Hybridization for *Salmonella* Detection," *Applied and Environmental Microbiology*, 2009, vol. 75, No. 5, pp. 1450-1455.

Cox, M. L., et al., Assessment of Fixatives, Fixation, and Tissue Processing on Morphology and RNA Integrity, *Experimental and Molecular Pathology*, 2006, vol. 80, pp. 183-191.

Daims, H., et al., "*Daime*, a Novel Image Analysis Program for Microbial ecology and Biofilm Research," *Environmental Microbiology*, 2006, vol. 8, No. 2, pp. 200-213.

Delong, E., et al., "Phylogenetic Stains: Ribosomal RNA-Based Probes for the Identification of Single Cells," *Science*, 1989, vol. 243, pp. 1360-1363.

Fuchs, B. M., et al., "Flow Cytometric Analysis of the In Situ Accessibility of *Escherichia coli* 16s rRNA for Fluorescently Labeled Oligonucleotide Probes," *Applied and Environmental Microbiology*, 1998, vol. 64, No. 12, pp. 4973-4982.

Hartmann, H., et al., "Rapid Identification of *Staphylococcus aureus* in Blood Cultures by a Combination of Fluorescence In Situ Hybridization Using Peptide Nucleic Acid Probes and Flow Cytometry," *Journal of Clinical Microbiology*, 2005, vol. 43, No. 9, pp. 4855-4857.

Kempf, V.A.J., et al., "Rapid Detection and Identification of Pathogens in Blood Cultures by Fluorescence In Situ Hybridization and Flow Cytometry," *International Journal of Medical Microbiology*, 2005, vol. 295, pp. 47-55.

Kempf, V.A.J., et al., "Fluorescent In Situ Hybridization Allows Rapid Identification of Microorganisms in Blood Cultures," *Journal of Clinical Microbiology*, 2000, vol. 38, No. 2, pp. 830-838.

Leach, K. M., et al., Same-Day Detection of *Escherichia coli* O157:H7 from Spinach by Using Electrochemiluminescent and Cytometric Bead Array Biosensors, *Applied and Environmental Microbiology*, 2010, vol. 76, No. 24, pp. 8044-8052.

Li, X., et al., "Improved Microscopic Identification of *Clavibacter michiganensis* subsp. *sepedonicus* Cells by Combining In Situ Hybridization with Immunofluorescence," *Letters in Applied Microbiology*, 1997, vol. 24, pp. 431-434.

Lim, D.V., et al., "Current and Developing Technologies for Monitoring Agents of Bioterrorism and Biowarfare," *Clinical Microbiology Reviews*, 2005, vol. 18, No. 4, pp. 583-607.

Oerther, D.B., de los Reyes III, F.L., Hernandez, M. and Raskin, L. "Simultaneous oligonucleotide probe hybridization and immunostaining for in situ detection of *Gordona* species in activated sludge" *FEMS Microbiol. Ecol.*, 1999, vol. 29, pp. 129-136.

Peters, R.P.H, et al., "Rapid Identification of Pathogens in Blood Cultures with a Modified Fluorescence In Situ Hybridization Assay," *Journal of Clinical Microbiology*, 2006, vol. 44, No. 11, pp. 4186-4188.

Ramage, G., et al., "Combined Fluorescent In Situ Hhybridisation and Immunolabelling of *Bacteroides fragilis*," *Journal of Immunological Methods*, 1998, vol. 212, pp. 139-147.

Shibutani, M., et al, "Methacarn Fixation: A Novel Tool for Analysis of Gene Expressions in Paraffin-Embedded Tissue Specimens," *Laboratory Investigation*, vol. 80, No. 2, pp. 199-208.

Shibutani, M. And Uneyama, C., "Methacarn: A Fixation Tool for Multipurpose Genetic Analysis from Paraffin-Embedded Tissues," *Methods in Enzymology*, 2002, vol. 356, pp. 114-125.

Simpson-Stroot, J.M., et al., "Monitoring Biosensor Capture Efficiencies: Development of a Model Using GFP-Expressing *Escherichia coli* O157:H7," *Journal of Microbiological Methods*, 2008, vol. 72, pp. 29-37.

Srinivasan, M., et al., "Effect of Fixatives and Tissue Processing on the Content and Integrity of Nucleic Acids," *American Journal of Pathology*, 2002, vol. 161, No. 6, pp. 1961-1971.

Wagner, M., et al., "Fluorescence In Situ Hybridisation for the Identification and Characterisation of Prokaryotes," *Current Opinion in Microbiology*, 2003, vol. 6, pp. 302-309.

Wallner, G., et al., "Optimizing Fluorescent In Situ Hybridization with rRNA-Targeted Oligonucleotide Probes for Flow Cytometric Identification of Microorganisms," *Cytometry*, 1993, vol. 14, pp. 136-143.

Wallner, G., et al., "Flow Sorting of Microorganisms for Molecular Analysis," *Applied and Environmental Microbiology*, 1997, vol. 63, No. 11, pp. 4223-4231.

Wellinghausen, N., et al., "Rapid Detection of *Brucella* spp. in Blood Cultures by Fluorescence In Situ Hybridization," *Journal of Clinical Microbiology*, 2006, vol. 44, No. 5, pp. 1828-1830.

\* cited by examiner

METHODS AND MATERIALS FOR CAPTURE ANTIBODY TARGETED FLUORESCENT IN-SITU HYBRIDIZATION (CAT-FISH)

CROSS-REFERENCE TO RELATED APPLICATIONS

The present application claims the benefit of U.S. Provisional Application Ser. Nos. 61/465,227, filed Mar. 16, 2011, and 61/428,468, filed Dec. 30, 2010, each of which is hereby incorporated by reference herein in its entirety, including any figures, tables, nucleic acid sequences, amino acid sequences, or drawings.

GOVERNMENT SUPPORT

This invention was made with government support under grant number W911SR-07-C-0084 awarded by the U.S. Army. The government has certain rights in the invention.

BACKGROUND OF THE INVENTION

Pathogen detection using biosensors is commonly limited due to the need for both sensitivity and specificity in detecting targets within the mixed populations present in complex samples (Lim et al., 2005). The relatively high detection limits inherent in most systems are influenced by many factors, including low target concentrations, poor capture efficiencies, non-target detection (false positives/negatives) and interference by organic/inorganic constituents, all of which precludes adequate detection (Simpson-Stroot et al., 2008). Additionally, for those systems using immunochemistry for target capture or reporting (e.g., antibody sandwich assays), non-target cross-reactivity issues can be problematic, and adequately specific antibodies are often not available.

Some of these limitations may be overcome by combining two different molecular signature techniques, which would bestow added confidence for identifying the presence of targeted pathogens—in particular, the use of specifically-targeted fluorescently-labeled 16S rRNA gene oligonucleotide probes in conjunction with specifically-targeted antibodies. The dual level specificity (nucleic acid and protein) allows two levels of accuracy for detection and/or confirmation, as well as addressing cross-reactivity. For example, if the antibody available for a given target cross-reacts with other bacteria (related or otherwise), it could still be used for antibody capture-dependent biosensors, as long as a labeled nucleic acid specific probe was used to generate the signal (as opposed to a labeled detector antibody). This probe would only provide fluorescent signal to the appropriate target. Thus, the binding of unlabeled non-target cells to the antibodies becomes a null issue as no signal is generated.

The use of fluorescence in situ hybridization (FISH) to phylogenetically identify microorganisms without cultivation based on either 16S or 23S rRNA has become a mainstay of microbial ecology since its introduction (DeLong et al., 1989; Amann et al., 1990; Amann, 1995; Amann et al., 2001; Wagner et al., 2003; Daims et al., 2005). FISH has also been reported as a rapid method for pathogen identification in clinical and food settings (Kempf et al., 2000; Hartmann et al., 2005; Kempf et al., 2005; Peters et al., 2006; Wellinghausen et al., 2006; Bisha and Brehm-Stecher, 2009; Bisha and Brehm-Stecher, 2009). Although the predominant FISH application has been to study microbial community structure and spatial arrangements on solid supports, some applications have explored its usefulness for flow cytometric analyses (Amann et al., 1990; Wallner et al., 1993; Wallner et al., 1997; Fuchs et al., 1998; Hartmann et al., 2005; Kempf et al., 2005). This adaptation to a liquid phase processing for flow cytometry lends itself to facilitating biosensor applications, provided that conditions allowing for both probe and antibody recognition are met.

Traditionally, samples to be processed by FISH are fixed with paraformaldehyde (PFA) to stabilize and preserve them (Daims et al., 2005). PFA acts as a strengthening agent on the membranes of Gram-negative bacteria by cross-linking proteins to prevent lysis during hybridization, but can make Gram-positive bacteria highly resistant to probe uptake (Leong, 1994; Daims et al., 2005). Additionally, this cross-linking activity, while giving stability and excellent conditions for FISH, can severely inhibit any subsequent immunochemistry. To circumvent these problems, combined bacterial applications of FISH and immunostaining have typically involved extensive antibody incubation times or involved processing steps to overcome the fixative effects (Aβmus et al., 1997; Li et al., 1997; Ramage et al., 1998; Oerther et al., 1999), limiting their utility for rapid and high-throughput testing situations.

As formaldehyde and its derivatives are well known in the histopathology community to inhibit molecular analyses (e.g., immunostaining, immunohistochemistry or nucleic acid analysis), alternative tissue fixatives have been explored that are more conducive to downstream processing (Baumgärtner et al., 1988; Leong, 1994; Shibutani et al., 2000; Srinivasan et al., 2002; Cox et al., 2006). Methacarn solution has been found to be a non-cross-linking protein-precipitating fixative that does not appear to affect polynucleotide or protein analysis of fixed tissues and usually will give superior immunohistochemical results (Shibutani and Uneyama, 2002). This success with tissues suggests that methacarn solution may also be successful with fixation of bacterial cells and lend itself to facilitating the use of FISH in combination with immunolabeling for biosensor detection.

In the work described herein, we demonstrate a modified liquid FISH processing method used in conjunction with capture antibody targeted detection (CAT-FISH) to increase the specificity for biosensor assays. Detection of pathogens in pure cultures and seeded matrices was demonstrated on a cytometric bead array biosensor, using bead-bound capture antibodies with FISH labeled cells. Since the applications of both FISH and immunochemistry have been well established for use with complex sample matrices, this method should be easily adapted to other bacteria and biosensor platforms. The use of FISH in conjunction with antibody based biosensor assays for pathogen detection has not been previously reported.

BRIEF SUMMARY OF THE INVENTION

The subject invention concerns materials and methods for detecting a target cell in a population. Methods of the invention comprise internally labeling cells via FISH using probes that target rRNA, such as 16S and/or 23S rRNA of prokaryotes, followed by binding of capture antibodies targeted (CAT) for specific cell surface epitopes. In one embodiment, the target cells are bacterial cells. In one embodiment, superparamagnetic beads and IMS-based separations were used as the platform for target capture in the present invention.

In the present invention, xMAP technology/cytometric bead array was modified and used for detection of the FISH labeled cells. In one embodiment, orange fluorescent superparamagnetic microspheres are conjugated to a specific antibody, the antibody-bead complex is used to draw FISH-labeled target cells out of solution, and the FISH-label is then read, e.g., by the specialized flow cytometer. The combination of CAT-FISH and xMAP technology allows elimination of the need for the reporter antibody step, thus simplifying the detection process, reducing non-specific background signal (improving signal to noise ratios) and reducing costs.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 1A and 1D) PFA treatment; FIGS. 1B and 1E) Methacarn treatment; FIGS. 1C and 1F) CAT-FISH treatment. Scale bar is 5 µm.

FIGS. 2A-2D. ELISA comparison of fixative effect on antibody binding for liquid FISH hybridized bacteria. FIG. 2A) Pre-hybridized *E. coli* O157:H7 fixed with methacarn or PFA and unfixed control; FIG. 2B) Post-hybridized fixed *E. coli* O157:H7 after liquid FISH treatment steps; FIG. 2C) Pre-hybridized *S. aureus* fixed with methacarn or PFA and unfixed control; FIG. 2D) Post-hybridized fixed *S. aureus* after liquid FISH treatment steps.

FIGS. 3A-3F. CAT-FISH dual labeled *E. coli* O157:H7 and *S. aureus*. FIG. 3A) *E. coli* labeled internally with EUB338 CY3 16S rRNA FISH probe; FIG. 3C) Merged A and B images; FIG. 3D) *S. aureus* labeled internally with EUB338 CY3 16S rRNA FISH probe; FIG. 3E) *S. aureus* labeled externally with biotin conjugated rabbit anti-*S. aureus* primary antibody and streptavidin conjugated fluorescein isothiocyanate (FITC) secondary antibody; FIG. 3F) Merged D and E images; Scale bar is 5 µm.

FIGS. 4A-4D. Cytometric bead fluorescence images with or without *E. coli* O157:H7. FIG. 4A) Standard assay with non-spiked PBS; FIG. 4B) Standard assay with non-spiked spinach rinse; FIG. 4C) Standard assay with *E. coli* O157:H7; FIG. 4D) CAT-FISH assay with *E. coli* O157:H7. Negative controls (no target and/or no reporter) are not shown due to lack of fluorescence. Scale bars are 10 µm.

BRIEF DESCRIPTION OF THE SEQUENCES

SEQ ID NO:1 is an oligonucleotide hybridization probe that can be used according to the present invention.

SEQ ID NO:2 is an oligonucleotide hybridization probe that can be used according to the present invention.

DETAILED DESCRIPTION OF THE INVENTION

The subject invention concerns materials and methods for detecting a target cell in a population. Methods of the invention comprise internally labeling cells via FISH in a liquid system using one or more detectably labeled probes that target rRNA, such as 16S and/or 23S rRNA of prokaryotes, followed by binding of capture antibodies targeted (CAT) for specific cell surface epitopes. In one embodiment, the target cells are bacterial cells. FISH methods and probes that target 16S rRNA are described in U.S. Pat. No. 7,771,941, the disclosure of which is incorporated by reference herein in its entirety.

The subject invention provides for detection of target cells in complex samples using the dual specificity provided by rRNA sequences (nucleic acid level specificity) and the epitope specific binding of antibodies (protein level specificity). The FISH methods are modified to allow for retaining samples in liquid form and to permit subsequent antibody binding to the target cell surface. As the targeted cells are internally labeled by the FISH probes, their capture by antibodies and subsequent detection are platform independent as long as the detector is capable of detecting the label, e.g., fluorescent signal in the appropriate wavelength. The detection methods allow for capture of FISH-labeled target cells onto antibody-coupled beads and subsequent detection using cytometric identification, in a multiplex capable format.

In one embodiment of a method of the invention, a sample to be tested for the presence of target cells therein is obtained. Optionally, cells in the sample can be centrifuged or otherwise isolated from the sample. The cells are then fixed in a solution that will allow for antibody binding after the FISH processing steps (e.g., a non-crosslinking fixative). In a specific embodiment, the cells are fixed with a methacarn solution. In one embodiment, following fixation, the cells can optionally be contacted with one or more lytic enzymes, such as lysozyme, lysostaphin, and/or nisin. After fixation, the cells are dehydrated optionally using ethanol washes and air drying. The cells are then contacted with a detectably labeled probe that targets an rRNA of the target cell under suitable hybridization conditions (FISH) and for an effective period of time. In one embodiment, the detectably labeled probe is an oligonucleotide. In another embodiment, the detectably labeled probe is a peptide nucleic acid probe. In one embodiment, the probe targets a 16S and/or 23S rRNA of a prokaryote. In a specific embodiment, the probe can be fluorescently labeled. Optionally, the cells are centrifuged after FISH and resuspended in a suitable buffer solution. The cells are then contacted with an antibody immobilized on a surface platform, wherein the antibody (or antibodies) is directed to one or more antigens on the surface of the target cell. The target cells bind to the antibodies immobilized on the surface platform. The bound target cells can be washed with a suitable medium or buffer. The bound target cells are then detected via detection of the labeled probe hybridized to rRNA of the target cells using any suitable detection means.

Antibodies of the invention can be immobilized on any suitable surface platform. Examples of surface platforms contemplated for use with the subject invention include, but are not limited to, beads (such as microbeads); microtiter plates; microarrays; fiber optic waveguides; planar array biosensors; and microfluidic chips. In an exemplified embodiment, the antibody is immobilized on a bead surface, such as a microbead. In a specific embodiment, the beads are composed of or comprise a material that can be attracted by a magnetic field. In one embodiment, the beads are magnetic or superparamagnetic beads. Beads useful in the present invention can be color coded using different ratios of different detectable labels or fluorescent molecules, e.g., orange fluorescent molecules. The detectable label or fluorophore of the bead can be different than the detectable label of the labeled probe. The target cells are bound to the beads via the antibody binding to the target cell antigens and then the beads are isolated or separated out from unbound material. In those embodiments where the beads can be attracted by a magnetic field, bound target cells can be separated from the unbound material by application of a magnetic field which collects and isolates the beads from the unbound material. In another embodiment, the beads can be sorted from materials using fluorescence activated cell sorting. The labeled probe bound to the target cell rRNA is then detected using suitable detection means. Optionally, the beads having target cells bound thereto can be washed and/or resuspended in a suitable medium or buffer prior to application of the detection means.

In one embodiment, a fixative solution useful in the subject invention is a methacarn solution. Methacarn solution has been found to be a non-cross-linking protein-precipitating fixative that does not appear to affect polynucleotide or protein analysis of fixed tissues and usually will give superior immunohistochemical results (Dotti et al. (2010); Shibutani and Uneyama (2002); Urieli-Shoval et al. (1992)). Other fixative solutions contemplated within the scope of the invention include, but are not limited to, ethanol, methanol, Carnoy's solution (e.g., 60% ethanol, 30% chloroform and 10% glacial acetic acid), and Histo-Choice® MB (AMRESCO, Inc., Solon, Ohio) (U.S. Pat. Nos. 5,429,797 and 5,439,667).

Oligonucleotide probes useful in the subject invention can be readily identified and prepared by an ordinarily skilled artisan. Oligonucleotide probes that bind to rRNA of a target cell have been identified and described in the art. In addition, an ordinarily skilled artisan can identify rRNA sequences of a target cell and can prepare oligonucleotide probes that will hybridize with specificity to those sequences. Databases for rRNA sequences and probes are available to the public (see, for example, Loy et al. (2007) and http://www.microbial-ecology.net/probebase; Ribosomal Database Project http://rdp.cme.msu.edu). In one embodiment, an oligonucleotide probe of the invention hybridizes with 16S and/or 23S rRNA of a prokaryote. In another embodiment, an oligonucleotide probe of the invention hybridizes with 18S and/or 28S rRNA of a eukaryote. Oligonucleotide probes of the invention can comprise one or more detectable labels. In one embodiment, an oligonucleotide probe comprises a dual label.

Detectable labels that can be used with a probe of the present invention include, but are not limited to, fluorescent moieties, chemiluminescent and bioluminescent reagents, enzymes, and radioisotopes. Fluorescent moieties include, but are not limited to, fluorescein, fluorescein isothiocyanate, Cascade Blue, rhodamine, dichlorotriazinylamine fluorescein, dansyl chloride, Texas Red, Oregon Green, cyanines (e.g., CY2, CY3, and CY5), umbelliferone, allophycocyanine or phycoerythrin. An example of a luminescent material includes luminol. Examples of bioluminescent materials include, but are not limited to, luciferin, green fluorescent protein (GFP), enhanced GFP (Yang et al., 1996), and aequorin. Enzymes that can be used include but are not limited to luciferase, beta-galactosidase, acetylcholinesterase, horseradish peroxidase, glucose-6-phosphate dehydrogenase, and alkaline phosphatase. If the detectable label is an enzyme, then a suitable substrate that can be acted upon by the enzyme can be used for detection and measurement of enzyme activity. In one embodiment, if the detectable label is a peroxidase, the substrate can be hydrogen peroxide ($H_2O_2$) and 3-3' diaminobenzidine or 4-chloro-1-naphthol and the like. Other substrates suitable for use with other enzymes are well known in the art. Isotopes that can be used include, but are not limited to, $^{125}I$, $^{14}C$ $^{35}S$, and $^{3}H$.

Antibodies that can be used in the subject invention can be genus or species specific to a target cell. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975).

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Examples of bacterial cells that can be detected using the present invention include, but are not limited to, *Nitrospira* spp., *Nitrosospira* spp., *Nitrobacter* spp., *Nitrosomonas* spp., *Clostridium* spp., *Bacillus* spp. (such as *Bacillus anthracis*), methanogenic archaea, coliforms (such as *E. coli*), *Salmonella* spp., *Bacteroides* spp., *Staphylococcus* spp., *Streptococcus* spp., *Neisseria* spp., *Haemophilus* spp., *Bordetella* spp., *Listeria* spp., *Mycobacterium* spp., *Shigella* spp., *Pseudomonas* spp., *Brucella* spp., *Treponema* spp., *Mycoplasma* spp., *Yersinia* spp., *Vibrionaceae* spp., *Chlamydia* spp., *Legionella* spp., *Escherichia* spp., *Acinetobacter* spp., *Burkholderia* spp., *Thiobacillus* spp., *Rickettsia* spp., *Sphinomonas* spp., *Francisella* spp., *Campylobacter* spp., and *Helicobacter* spp.

In one embodiment, an oligonucleotide probe of the invention may be one that specifically hybridizes with at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of the target sequence (such as the 5' or 3' end of precursor 16S rRNA; or the interior region of both precursor 16S rRNA and mature 16S rRNA). Various degrees of stringency of hybridization can be employed. The more stringent the conditions, the greater the complementarity that is required for duplex formation. Stringency can be controlled by temperature, salt concentration, chaotropic agent concentration and the like. Preferably, hybridization is conducted under low, intermediate, or high stringency conditions by techniques well known in the art, as described, for example, in Keller and Manak (1987) or Maniatis et al. (1982).

In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al. (1983)).

$$Tm = 81.5° C. + 16.6 \log(Na^+) + 0.41(\% \, G+C) - 0.61(\% \, formamide) - 600/\text{length of duplex in base pairs}.$$

Washes are typically carried out as follows:
(1) twice at room temperature for 15 minutes in 1×SSPE, 0.1% SDS (low stringency wash);
(2) once at $T_m - 20°$ C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$$T_m(° C.) = 2(\text{number } T/A \text{ base pairs}) + 4(\text{number } G/C \text{ base pairs}) \, (\text{Suggs et al. (1981)}).$$

Washes can be carried out as follows:
(1) twice at room temperature for 15 minutes 1×SSPE, 0.1% SDS (low stringency wash);
(2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Intermediate: 0.2× or 1×SSPE, 65° C.

High: 0.1×SSPE, 65° C.

Samples contemplated within the scope of the invention include, but are not limited to, environmental (e.g., water, soil, slurry, sludge, gas, liquid, vapor, etc.) and biological samples. Biological samples can be obtained from an individual. The biological sample may be obtained by any method known in the art. Samples may be collected at a single time point or at multiple time points from one or more tissues or bodily fluids. The tissue or fluid may be collected using standard techniques in the art, such as, for example, tissue biopsy, blood draw, or collection of secretia or excretion from the body. Examples of suitable bodily fluids or tissues from which an infectious agent, or component thereof, may be isolated include urine, blood, intestinal fluid, edema fluid, saliva, lacrimal fluid (tears), inflammatory exudate, synovial fluid, abscess, empyema or other infected fluid, cerebrospinal fluid, pleural effusions, sweat, pulmonary secretions, seminal fluid, feces, bile, intestinal secretions, or any infected tissue including, but not limited to liver, intestinal epithelium, spleen, lung, pericardium, pleura, skin, muscle, synovium, cartilage, bone, bone marrow, thyroid gland, pancreas, brain, prostate, ovaries, endometrium, uterus, uterine cervix, testes, epididymis, bladder wall, kidney, adrenal, pituitary gland, adipose cells/tissue, omentum, or other cells and tissue. The frequency of obtaining one or more biological samples can vary.

A surface platform can have a fixed organizational support matrix that preferably functions as an organization matrix, such as a microtiter tray. Solid support materials include, but are not limited to, glass, polacryloylmorpholide, silica, controlled pore glass (CPG), polystyrene, polystyrene/latex, polyethylene, polyamide, carboxyl modified teflon, nylon and nitrocellulose and metals and alloys such as gold, platinum and palladium. The solid support can be biological, non-biological, organic, inorganic, or a combination of any of these, existing as beads, particles, strands, precipitates, gels, sheets, tubing, spheres, containers, capillaries, pads, slices, films, plates, slides, etc., depending upon the particular application. Other suitable solid substrate materials will be readily apparent to those of skill in the art. The surface of the solid substrate may contain reactive groups, such as carboxyl, amino, hydroxyl, thiol, or the like for the attachment of nucleic acids, proteins, etc. Surfaces on the solid substrate will sometimes, though not always, be composed of the same material as the substrate. Thus, the surface can be composed of any of a wide variety of materials, for example, polymers, plastics, resins, polysaccharides, silica or silica-based materials, carbon, metals, inorganic glasses, membranes, or any of the above-listed substrate materials.

The subject invention also concerns kits comprising in one or more containers: a probe that can bind to or hybridize with an rRNA of a target cell, and optionally a surface platform that can have an antibody attached thereto. In one embodiment, a kit comprises a detectably labeled oligonucleotide probe that can hybridize with the target cell rRNA. In one embodiment, a probe of the kit binds to or hybridizes with a 16S and/or 23S rRNA of a target cell. In one embodiment, the kit further comprises an antibody, or an antigen binding fragment thereof, that can bind to one or more surface antigens on the surface of the target cell. In one embodiment, the antibody is a monoclonal antibody, or an antigen binding fragment thereof. In another embodiment, the antibody is a polyclonal antibody, or an antigen binding fragment thereof. In one embodiment, the kit further comprises a fixative solution for fixing cells, wherein the fixative solution allows for antibody binding to one or more antigens on the surface of the cells. In a further embodiment, the fixative solution is a non-cross linking fixative. In a specific embodiment, the fixative solution is a methacarn solution. In one embodiment, the surface platform provided in the kit is a bead, such as a microbead. In a further embodiment, the bead can be attracted by a magnetic field. In a further embodiment, the bead is a magnetic or super paramagnetic bead. In one embodiment, the bead contains a detectable label or fluorophore. In one embodiment, the probe is labeled with a fluorescent label, a chemiluminescent reagent, a bioluminescent reagent, an enzyme, or a radioisotope. In one embodiment, the kit further comprises one or more lytic enzymes. Kits of the invention can optionally include physiologically acceptable carriers and/or diluents. In one embodiment, a kit of the invention includes instructions or packaging materials that describe how to use the components of the kit for detection of a target cell. Containers of the kit can be of any suitable material, e.g., glass, plastic, metal, etc., and of any suitable size, shape, or configuration.

Materials and Methods

Microorganisms

*Escherichia coli* O157:H7 (ATCC 35150) and *Staphylococcus aureus* (ATCC 25923) were cultured at 37° C. with shaking in brain heart infusion broth (BHI) (Difco, Becton Dickinson, Franklin Lakes, N.J.). Cells were cultured for ~18 h prior to experiments and then diluted 1:100 in fresh BHI and incubated as described. Cells were harvested at 0.8 O.D. (600 nm) and washed once with 1× phosphate buffered saline (PBS ~11.9 mM phosphate buffer, 137 mM sodium chloride, 2.7 mM potassium chloride, pH 7.4 (Fisher BioReagent, Suwanee, Ga.)). Cell pellets were then fixed immediately (PBS samples) or diluted into complex matrix prior to fixation.

Fixation

Harvested bacteria were fixed by one of two methods: Control cells were fixed with 4% ice-cold paraformaldehyde (PFA) for 2 hrs at 4° C., collected by centrifugation (9,000× g) for 90 s, decanted and resuspended in 50% (v/v) ethanol in 1×PBS according to standard FISH protocols (Daims et al., 2005). Test cells were fixed with methacarn solution (6:3:1 parts absolute methanol, chloroform, and glacial acetic acid) made fresh daily (Leong, 1994). All manipulations involving the methacarn solution were performed in a chemical hood. Cell pellets were resuspended in methacarn, incubated at room temperature (22° C.) for 10 min, collected by centrifugation (9,000×g) for 90 s, decanted, and washed once in 80% (v/v) ethanol and once in 100% ethanol. Cell pellets were dried in the dark via rotation for 20 min at 46° C. to drive off remaining ethanol (Enviro-Genie, Scientific Industries, Inc., Bohemia, N.Y.). Samples containing spinach rinse (spiked with *E. coli* O157:H7 or un-amended) were processed in the same manner. For *Staphylococcus* samples, prior to alcohol dehydration steps, cells were treated with lytic agents as follows: after centrifugation, cells were washed once in 10 mM Tris HCl pH 8.0, centrifuged and resuspended in lysozyme (1 mg/ml in 10 mM Tris HCl pH. 8.0) and incubated 15 min at 30° C.; then cells were collected as described and resuspended in either lysostaphin (10 µg/ml in 10 mM Tris HCl pH 8.0) and incubated 5 min at 30° C. or nisin (0.1 g of 2.5% powder in 10 ml 0.02N HCl pH 2.0) diluted into PBS for final concentration of 25 µg/ml).

Liquid Fluorescence In Situ Hybridization (LQ-FISH)

Fluorescently-labeled oligonucleotide hybridization probes targeting the 16S rRNA for the domain *Eubacteria* (EUB338; 5' gctgcctcccgtaggagt 3' SEQ ID NO:1) and species *S. aureus* (SAU349; 5' gaagcaagcttctcgtccg 3' SEQ ID NO:2) were obtained from Molecular Probes (Invitrogen, Carlsbad, Calif.) and labeled with either Alexa Fluor 532 or Cy3 at the 5' end (Loy et al., 2007). Alexa Fluor 532 labeled probe was used for cytometric bead array assays, and Cy3 labeled probe was used for optimization assays, image capture and image analysis. The probes were diluted to 50 ng/µl with $dH_2O$, and stored in 100-µl aliquots at −20° C. in the dark. Fixed and dried sample pellets (pure cultures or spiked matrix) were resuspended in 200 µl of hybridization buffer containing the labeled probe at a final concentration of 5 ng/µl. The hybridization buffer also contained 20% (v/v) formamide, 0.9 M NaCl, 0.1% SDS and 100 mM Tris HCl (pH 7.0) (Daims et al., 2005). Hybridization was conducted in the dark for 1 h in a 46° C. water bath. Subsequently, samples were centrifuged (9,000×g) for 90 s, the supernatant was removed, and cells were resuspended in 500 µl of pre-warmed washing buffer followed by 10 mM incubation in a 48° C. water bath in the dark. The washing buffer contained 215 mM NaCl, 20 mM Tris HCl (pH 7.0) and 5 mM EDTA (Daims et al., 2005). After washing, samples were centrifuged and the supernatant removed. Treated pellets were resuspended in PBS for downstream processing (microscopy, antibody labeling, or immunomagnetic capture and cytometric analysis).

Standard Fluorescence In Situ Hybridization

Variations in oligonucleotide conferred fluorescence intensity based upon fixative affect were measured. Cells fixed by either PFA or methacarn were placed on 10-well heavy Teflon coated microscope slides (Cel-Line Associates, New Field, N.J.) and processed by standard FISH protocols (Amann et al., 1990; Oerther et al., 2000) using the Cy3-labeled EUB338 probe. Lytic agents were applied to the *Staphylococcus* samples as described in the section entitled "Fixation." The hybridization step was 1 h and the washing step was 30 min. Cells were counterstained with 4',6-diamidino-2-phenylindole (DAPI) at a concentration of 1 µg/mL for 1 minute, rinsed with $dH_2O$, air dried, and mounted with Cargille immersion oil (Type FF, Cedar Grove, N.J.) and a cover slip.

Antibody Binding Assays

Fixed cells were used in adsorption enzyme linked immunosorbent assays (ELISA) to compare antibody recognition after the different fixation techniques. Bacteria were fixed with either PFA or methacarn as described above and split, with half used as controls and half processed alike through the entire liquid FISH procedure. Additional controls consisted of untreated cells that were harvested and stored on ice in PBS from the same initial test cultures. After treatments, cells were enumerated by direct microscopic count, normalized to $1 \times 10^8$ cells/ml and serially diluted to $10^3$ cells/ml in PBS. Preliminary experiments indicated that cell concentrations below $10^2$ cells/ml did not produce measurable signal and were omitted from further tests (data not shown). Cells were then applied in triplicate to an ELISA plate, incubated at 4° C.~18 hrs and processed using a QuantaBlu Fluorogenic Peroxidase kit (PIERCE, Rockford, Ill.) according to manufacturer's instructions with the following exceptions: volumes for each step were normalized to 100 μl and incubation times were reduced to 30 min each. Reporter antibodies included affinity purified peroxidase labeled polyclonal goat anti-*E. coli* O157:H7 (1 μg/ml) (KPL, Gaithersburg, Md.), purified rabbit anti-*S. aureus* (10 μg/ml) (AbD Serotec, Raleigh, N.C.) and affinity purified peroxidase labeled goat anti-rabbit (1 μg/ml) (KPL). ELISA plates were washed using an $EL_x50$ auto-strip washer (Bio-Tek Instruments Inc., Winooski, Vt.) and end product detection performed on a SpectraMax GeminiXS Fluorometer (Molecular Devices, Silicon Valley, Calif.). Results are reported as signal to noise (S/N) ratios for test samples versus PBS, where an S/N ratio above 3 indicates a positive detection result.

Simultaneous FISH and Reporter Antibody Labeling

*E. coli* O157:H7 and *S. aureus* samples were individually fixed in methacarn and processed according to the liquid FISH method described in the section entitled "Liquid fluorescence in situ hybridization (LQ-FISH)" either with or without Cy3-labeled EUB338 probe. Treated cells were resuspended in 500 μl PBS containing either 4 μg/ml goat anti-*E. coli* O157:H7 (KPL—for *E. coli* O157:H7 samples) or 4 μg/ml biotin conjugated rabbit anti-*S. aureus* (AbD Serotec—for *S. aureus* samples), and incubated at room temperature for 30 min in the dark with end over end rotation (24 rpm). The cells were recovered by centrifugation (9,000×g for 90 s) and washed once in 500 μl PBS with 5 min end over end rotation. *E. coli* and *S. aureus* samples were then resuspended in 500 μl PBS containing 2 μg/ml Cy2-labeled donkey anti-goat (Jackson ImmunoResearch Laboratories, Inc., West Grove, Pa.) or 2 μg/ml streptavidin conjugated fluorescein isothiocyanate (FITC) (Jackson ImmunoResearch), respectively. Cells were incubated at room temperature for 30 min in the dark with end over end rotation, washed, resuspended in 100 μl PBS, and visualized using an epifluorescent microscope.

Cytometric Assays

A method was developed to incorporate immunomagnetic separation (IMS) with cytometric bead arrays for direct detection of FISH labeled cells (IMS-CAT-FISH) using a specialized flow cytometer. This method is a modification to standard cytometric bead array (CBA) assays, which rely on a labeled detector antibody for target detection. MagPlexC magnetic microbeads (6.5±0.2 μm, fluorescence region 33, Luminex, Austin, Tex.) were used for all assays, and for all manipulations beads were separated from liquid solutions using the 3-in-1 Magnetic Particle Separator (PureBiotech, LLC, Middlesex, N.J.). Magnetic microspheres were coupled to goat anti-*E. coli* O157:H7 antibody (KPL) or rabbit anti-*S. aureus* (AbD Serotec) using the amine coupling kit (BioRad, Hercules, Calif.), per the manufacturer's instructions and stored at 4° C. until used.

Coupled magnetic microspheres were used to capture target cells from sample suspensions following the LQ-FISH procedure. Antibody-coupled microbeads (1,000 per sample) were added to 1 ml of sample and briefly mixed by vortex action on low setting. Mixed samples were centrifuged (6,000×g, 60 s) and target allowed to bind during a 5 min stationary incubation at 22° C. Samples were briefly mixed after incubation and beads were separated from the supernatant. Recovered beads were washed twice with 500 μl PBS containing 0.05% Tween 20 (PBST) in the dark using 5 min rotations. After washing steps, beads were separated from the sample supernatant and resuspended in 100 μl PBST. Beads were placed into 96-well round-bottom plates, and analyzed using the Bio-flex 200 reader (BioRad), per the manufacturer's instructions using the high PMT setting. Fluorescence signals were expressed as the mean fluorescence intensity of 100 beads per well.

Positive signals were determined using signal above limit of detection (SALOD) values. SALODs were calculated by taking the average sample signal and subtracting the limit of detection (LOD) value. The LOD value was calculated by averaging sample blanks and adding three times the standard deviation of the sample blanks. All experiments were performed in duplicate or triplicate.

Simulation of Complex Testing Situations

Spinach Rinse Matrix Preparation

Spinach rinse was generated to simulate a field wash sample as *E. coli* O157:H7 contamination is a concern in commercial produce products. Fresh bundled spinach was purchased from a local wholesale market (Tampa, Fla.) and processed within one day. Spinach rinse was generated and stored at −20° C. until used. Rinses were tested for background *E. coli* O157:H7 contamination according to established FDA-BAM procedures (Feng, 1998), and determined to be devoid of endogenous *E. coli* O157:H7 prior to initiation of experiments. Serially diluted samples were plated on BHI agar using the spread plate method to determine microbial background loads.

Prior to IMS-CAT-FISH, *E. coli* O157:H7 was diluted into spinach rinse, mixed 1:1 with 2× modified buffered peptone water with pyruvate (mBPWp), (Feng, 1998), and enriched overnight at 42° C., statically. After enrichment, spiked and un-spiked samples were plated onto CT-SMAC agar to verify growth in spiked samples and absence of target in controls. Before sampling, enriched samples were mixed briefly and allowed to stand for 1 min to allow for sand and large particulates to settle out. Samples for analysis were collected from the resultant supernatant, and processed for IMS-CAT-FISH, as described.

Blood Cultures

Citrated sheep blood (Fisher Scientific) was used as a surrogate for human blood. Blood samples were spiked with *S. aureus* at concentrations of ~2 CFU/ml (verified by plate counts on BHI agar), and diluted 1:5 into BACTEC-derived blood culture media, which was prepared in-house and contained 3% soybean-casein digest, 0.3% yeast extract, 0.01% beef extract, 0.1% sucrose, 0.0005% hemin, 0.00005% menadione, 0.001% Pyridoxal HCL, 0.04% sodium bicarbonate, and 0.035% sodium polyanetholsulfonate (all w/v). Samples were enriched overnight at 37° C., with aeration, and plated on BHI agar to verify bacterial growth in spiked samples, and absence of bacteria in non-spiked samples. 500 ul of the blood culture sample was used for each assay. The sample was mixed with 500 ul water and incubated for 5 minutes at room temperature to permit lysis of remaining erythroid cells. Samples were then centrifuged to pellet bacteria, re-suspended in 1 ml PBS, and processed according to the IMS-CAT-FISH procedure. Prior to IMS capture, samples were diluted 1:100 in order to dilute particulates resulting from remaining blood components.

Microscopic Imaging and Data Analysis

Samples for image analysis were placed on 10-well microscope slides (Cd-Line) and either observed under wet mount or air-dried. Air dried cells were mounted with Cargille immersion oil (Type FF) and a cover slip. Oligonucleotide and/or antibody conferred fluorescence were visualized with upright epifluorescence microscopes, either a Leitz DiaPlan (Heerbrugg, Switzerland) or an Olympus BX60F (Center Valley, Pa.). Digital images were captured using Spot-FLEX CCD cameras and image modifications (for publication purposes only) were performed using Spot Software 4.6 (Diagnostic Instruments, Inc., Sterling Heights, Mich.). Image modifications consisted of cropping, scale bar calibrations and pixel multiplicative brightness adjustments. Brightness adjustments were scaled up a factor of 2 or 3 dependant upon image series, however within each series the multiplicative factor was the same, so that relative intensities were comparable. All data analysis was performed on raw images without modifications. Fluorescent images were evaluated with the daime 1.3.1 software package (Daims et al., 2006). Measure objects analysis calculated the number of cells detected, as well as the mean fluorescent intensity and standard deviations for each cell. SIGMA-PLOT 10 (Systat Software, Inc., San Jose, Calif.) was used for graphic analysis. Student's t test was used to determine if significant differences occurred between fixative types.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Optimization of Processing Conditions

Preliminary evaluations of multiple fixatives and conditions, including standard FISH fixation with PFA, did not facilitate sufficient antigen-antibody binding as required for target capture and detection on biosensors (data not shown). Experiments attempting to ascertain antigen-antibody binding capabilities for stored PFA fixed *E. coli* cells were unsuccessful in producing any antibody binding (data not shown). Thus all subsequent experiments used "fresh" fixed cells for evaluation purposes, in that cells were processed immediately after fixation steps without holding or storage. Methacarn fixation was the most promising candidate for both fluorescence and antibody binding and was subsequently optimized for use in the LQ FISH protocol.

Example 2—Influence of Fixative Upon Fluorescent Signal

*E. coli* O157:H7 and *S. aureus* were fixed in either methacarn or PFA to determine if methacam fixation produced cells capable of binding probe and emitting fluorescence signals comparable to standard protocols. Cells from both fixative treatments (methacarn and PFA) were mounted on slides and subjected to standard FISH. In addition, cells were processed by the LQ-FISH method using methacarn fixation, and spotted onto separate slides (FIG. 1). Relative fluorescence intensity means for *E. coli* O157:H7 cells (200 per treatment) were: 61±12 for PFA, 68±11 for methacarn and 58±10 for LQ-FISH. Analyses indicated that there were no significant differences between the PFA and LQ-FISH treatments, but the methacarn treated cells were significantly brighter ($p \leq 0.0004$) than both PFA and LQ-FISH cells. Relative fluorescence intensity means for *S. aureus* cells (150 per treatment) were: 48±14 for PFA, 56±18 for methacarn and 100±28 for LQ-FISH. Analyses indicated that the PFA treated cells were significantly dimmer ($p \leq 0.003$) than both methacarn and LQ-FISH cells, and LQ-FISH treated cells were significantly brighter than the slide based methacarn treated cells ($p \leq 0.003$).

Example 3—Influence of Fixative Upon Antibody Binding

Figure 1A:
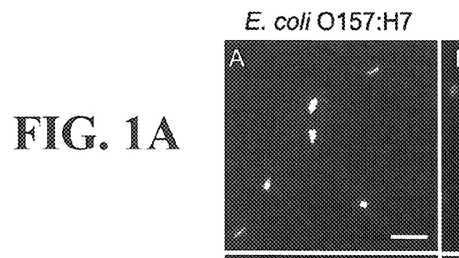
FIGS. 1A-1F. Comparison of relative fluorescence intensities for *E. coli* O157 and *S. aureus* treated with different fixatives. All cells were labeled with EUB338 Cy3 rRNA FISH probe. Cells fixed with either PFA or methacarn were fixed prior to mounting on slides for FISH processing. Cells treated via CAT-FISH were mounted on slide after the process was complete.
Figure 1B:
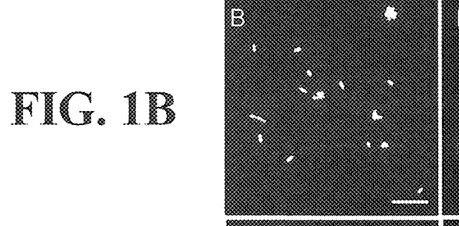
Figure 1C:
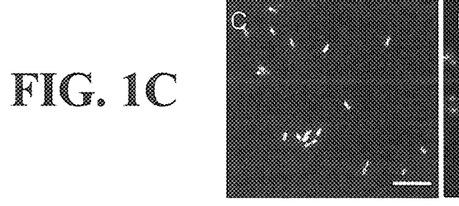
Figure 1D:
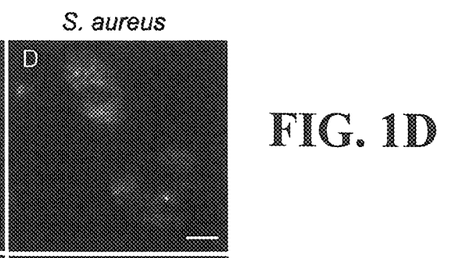
Figure 1E:
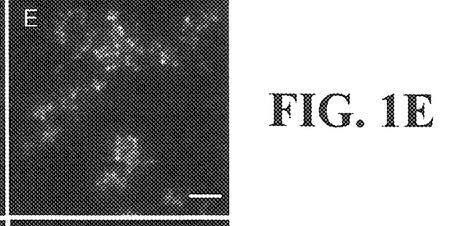
Figure 1F:
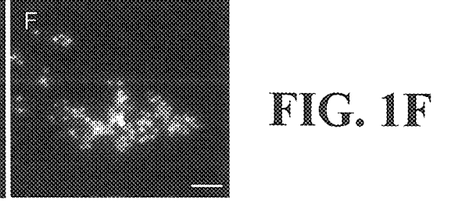
Figure 2A:
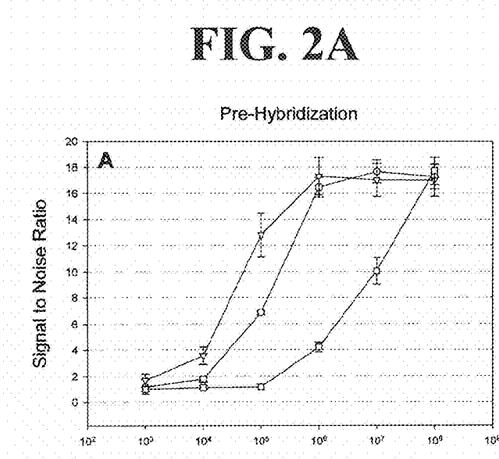
Figure 2B:
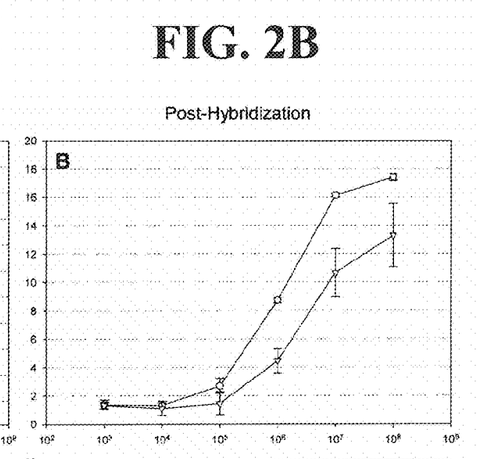
Figure 2C:
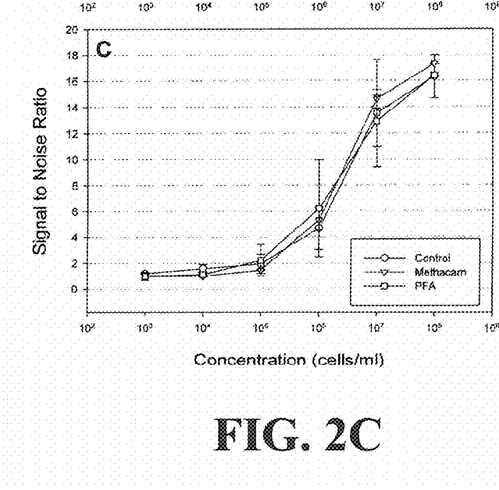
Figure 2D:
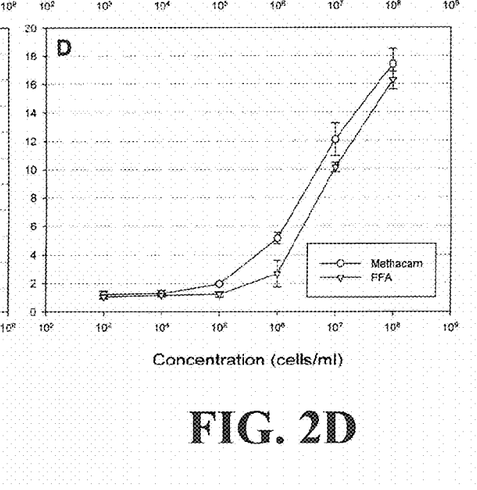
Figure 3A:
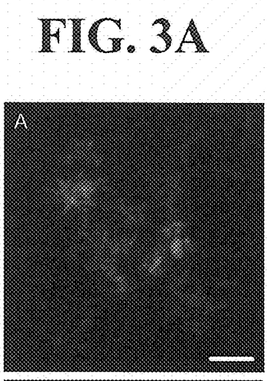
Figure 3B:
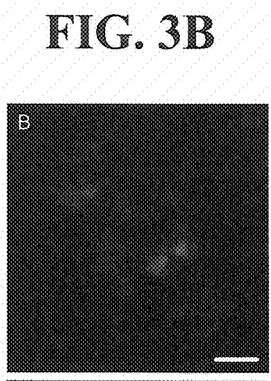
FIG. 3B) *E. coli* labeled externally with goat anti-*E. coli* O157:H7 primary antibody and rabbit anti-goat CY2 labeled secondary antibody.
Figure 3C:
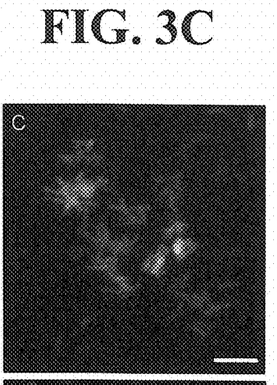
Figure 3D:
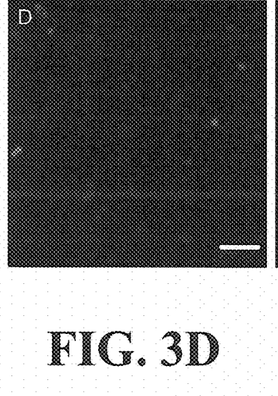
Figure 3E:
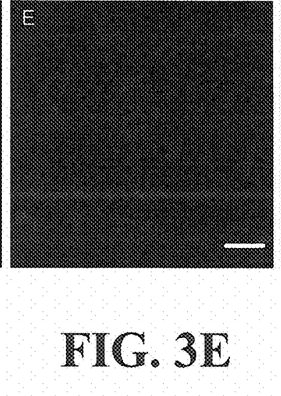
Figure 3F:
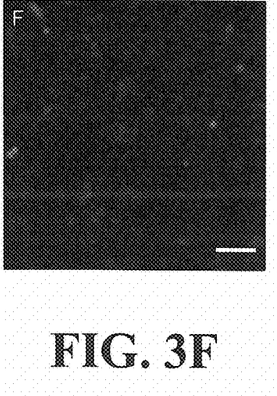

Adsorbent ELISAs were used to evaluate PFA and methacarn fixation effects. In addition, fixed cells were subjected to further hybridization conditions (LQ FISH) to determine the effect of hybridization treatments on antibody binding for *E. coli* O157:H7 and *S. aureus* (FIG. 2). Antibody binding was significantly reduced for PFA fixed *E. coli* as compared to control (non-fixed) and methacarn fixed cells for all concentrations below $10^8$ cells/ml (FIG. 2A). Positive S/N ratios were observed for methacarn, control, and PFA at $10^4$, $10^5$, and $10^6$ cells/ml, respectively. Methacarn treatment achieved better binding than controls at concentrations below $10^5$ cells/ml and showed no difference at higher concentrations. After LQ-FISH hybridization treatments, methacarn treated cells produced higher S/N ratios than PFA treated cells; however, the minimum concentration producing a positive signal was one log higher as compared to non-hybridized cells (FIG. 2B). No change in minimum concentration was observed for the PFA treated cells after hybridization. Antibody binding for *S. aureus* produced no significant differences between controls and methacarn or PFA fixed cells, and positive S/N ratios were achieved at $10^6$ cells/ml for all conditions (FIG. 2C). After hybridization, the methacarn fixed cells produced slightly higher S/N ratios, but were not significantly different from PFA samples. (FIG. 2D).

Example 4—Simultaneous Visualization of Oligonucleotide and Antibody Fluorescence Both labeling methods were used in conjunction to examine labeling coverage after methacarn fixation with LQ-FISH hybridization. *E. coli* O157:H7 and *S. aureus* were simultaneously labeled with rRNA probes and antibodies and generated signals that were sufficient for microscopic visualization (FIG. 3). Appropriate un-labeled controls were included (±probe and/or antibody) and verified (data not shown). Visual examination of *E. coli* cells indicated that they were uniformly labeled with both CY3 FISH probe and CY2 antibodies, providing ample coverage for dual level specificity detection. *S. aureus* cells also exhibited dual labeling, but the signal intensities appeared to be more variable for both fluorescent markers.

Example 5—Immunomagnetic Cytometric Bead Array Detection

A cytometric bead array biosensor was selected as an example platform to demonstrate the utility of the dual specificity target detection. Cells were labeled using LQ-FISH and captured by IMS using antibody-coupled magnetic cytometric array microspheres (IMS-CAT-FISH). Bead-associated fluorescence signal was then determined using the cytometric array reader. Initially, limit of detection assays for *E. coli* O157:H7 and *S. aureus* were performed in PBS, and microscopic evaluation of *E. coli* O157:H7 was used to visually verify labeling and capture. Utility of the method was subsequently verified using a more complicated testing matrix appropriate for each organism. In addition, *S. aureus* limit of detection assays were performed using either species specific lytic treatments (lysostaphin) or general gram-positive lytic treatment (nisin), incorporated into the LQ-FISH procedure.

Example 6—*E. coli* O157:H7 Detection Assays

We previously reported that standard cytometric bead array (IMS-CBA) assays using labeled detector antibodies are useful for rapid detection of *E. coli* O157:H7 in both PBS and a more complex testing scenario (raw spinach testing via enrichment of rinse samples) (Leach et al., 2010). However, in spinach rinse enrichment samples, some non-specific background signals were encountered, suggesting the need for a more specific detection procedure (Leach et al., 2010). Toward this end, CAT-FISH was applied.

Figure 4A:
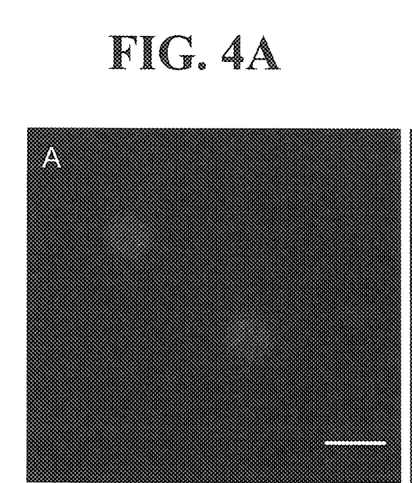
Figure 4B:
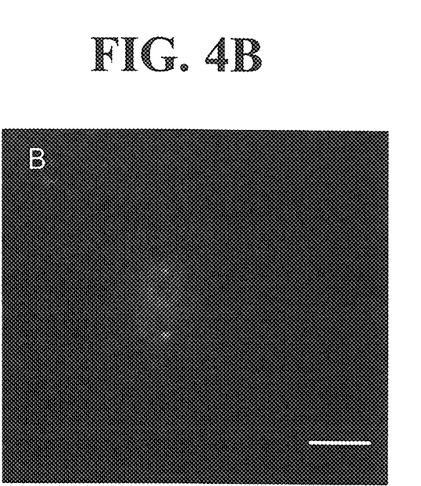
Figure 4C:
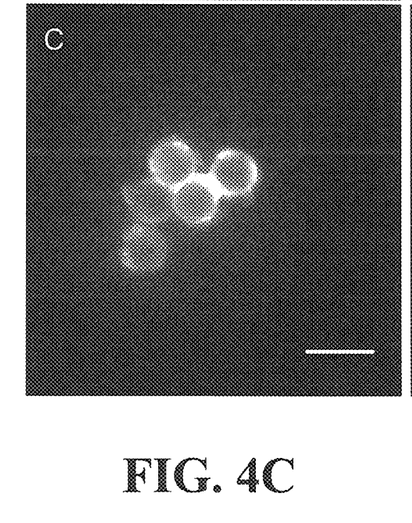
Figure 4D:
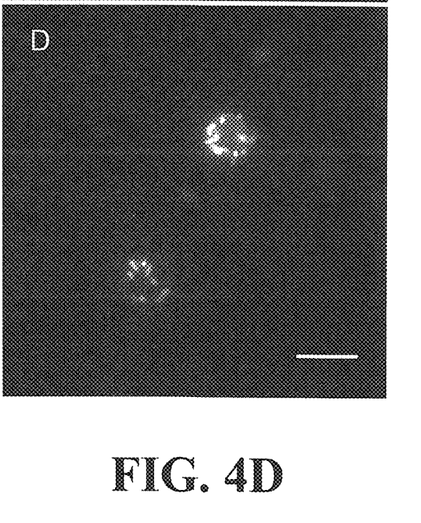

Microscopic evaluation was first conducted to evaluate target capture and labeling for both the standard IMS-CBA assay (antibody label) and the IMS-CAT-FISH method (FISH label). All samples (bead only controls, un-spiked PBS blanks, spiked PBS samples, and un-spiked spinach rinse blanks) were spotted onto slides and examined (FIG. 4). Beads incubated without target or reporter produced no detectable signal in either assay (not shown). Detector-associated signal for PBS blanks was absent from CAT-FISH treatments (i.e., no labeled cells present, not shown), but a dim signal was visible after processing according to standard array assay method (FIG. 4A). Beads incubated with control cells produced highly visible signal for both treatments. *E. coli* detected with the standard assay produced images with visible halos surrounding the surface of the captured cells, corresponding to the binding of labeled detector antibody to bead-capture cells. Labeled cells were easily distinguishable from the bead surfaces (FIG. 4C). *E. coli* cells detected with CAT-FISH produced images of solidly labeled cells bound to the surface of the beads (FIG. 4D). Non-spiked spinach blanks treated with CAT-FISH produced no detectable signal (not shown). Interestingly, there was observable signal on beads after the standard assay was performed on the un-spiked rinse. Fluorescence images displayed relatively large patches of labeled non-target particulate material attached to the cytometric array beads (FIG. 4B), thus demonstrating non-specific binding of spinach debris to the beads and the reporter antibody.

As microscopic evaluation indicated successful labeling and capture, a cytometric array biosensor (BioPlex 200) was used to evaluate target signals obtained using the IMS-CAT-FISH assay. Detection was sporadically observed at $10^3$ cells/ml and routinely observed at $10^4$ cells/ml (Table 1). A one log increase in signal strength was observed for each log increase in cell concentration until saturation was reached at $10^6$ cells/ml, after which no significant increases were observed. These detection limits are similar to those previously reported for the standard cytometric array assay (Kim et al., 2009; Kim et al., 2010; Leach et al., 2010) using a reporter antibody.

Next, the ability of the CAT-FISH dual labeling technique to mitigate matrix and antibody cross-reactivity problems was tested using enriched spinach rinse cultures. Two independent batches of spinach rinse were prepared according to the standard FDA-BAM protocol (Feng, 1998), and either left un-spiked or spiked with 0.9 CFU/ml *E. coli* O157:H7. After overnight enrichment, all samples were processed according to the CAT-FISH method, and FISH-labeled target cells were captured using anti-*E. coli* O157:H7 coupled magnetic cytometric array beads. Average relative fluorescent signals reported were 21.4+/−2.3 for PBS controls (n=3), 26.1+/−6.2 for un-spiked samples (n=12), and 583.1+/−200.6 (n=12) for spiked samples.

Example 7—*S. aureus* Detection Assay

*S. aureus* samples were treated with either a species specific or a generalized lytic agent to improve probe accessibility. Both were demonstrated as potential modifications of the assay, dependent upon whether the presence of *Staphylococcus* species is suspected (e.g., in blood samples gram positive cocci growing in clusters are assumed to be *Staphylococcus* species). PBS was spiked with targeted concentrations of $5 \times 10^7$ cells/ml *S. aureus* (direct count) and serially diluted to $10^1$ cells/ml with PBS. Final spike concentrations were confirmed by BHI plate count at $4.9 \pm 1.3 \times 10^7$ CFU/ml.

IMS-CAT-FISH assays produced consistent positive signal for all cell concentrations greater than $10^3$ cells/ml for both lysostaphin and nisin (Table 1). Control cells (absent probe) did not produce any positive signals. A one log increase in signal strength was observed for each log increase in cell concentration until saturation was reached at $10^6$ cells/ml, after which signal decreases were observed. A two-fold higher signal per concentration was generated using the *Staphylococcus* specific lysostaphin than was observed with the nisin.

As a further test for process utility, *S. aureus* was spiked into sheep blood at approximately 2 CFU/ml (verified by viable counts) to simulate a low-level bloodstream infection. Samples were cultured overnight according to standard blood culture practices and further processed, as described. In preliminary experiments, antibody cross-reactivity for non-*aureus Staphylococcus* species was observed (not shown), so the dual-level specificity allowed by CAT-FISH was demonstrated through the use of an *S. aureus*-specific probe. Two independent blood culture samples were each processed in triplicate according to the IMS-CAT-FISH method. The average relative fluorescent signals generated after capture were 35.2+/−2.1 for buffer controls (n=3), 32.4+/−4.3 for un-spiked blood controls (n=6), and 562.2+/−106.4 for *S. aureus* samples (n=6).

TABLE 1

CAT-FISH Detection of *E. coli* O157:H7 or *S. aureus* in PBS using a cytometric bead array biosensor.

| | | | *S. aureus* | | | |
|---|---|---|---|---|---|---|
| | *E. coli* O157:H7 | | Lysostaphin | | Nisin | |
| | Signal | SALOD[a] | Signal | SALOD | Signal | SALOD |
| PBS Buffer | 13.9 ± 1.2 | 17.3[b] | 32.7 ± 2.5 | 40.3[b] | 32.7 ± 2.5 | 40.3[b] |

TABLE 1-continued

CAT-FISH Detection of *E. coli* O157:H7 or *S. aureus* in PBS using a cytometric bead array biosensor.

| | E. coli O157:H7 | | S. aureus | | | |
|---|---|---|---|---|---|---|
| | | | Lysostaphin | | Nisin | |
| | Signal | SALOD$^a$ | Signal | SALOD | Signal | SALOD |
| $10^1$/ml | — | — | 31.9 ± 3.5 | −8.3 | 31.2 ± 4.8 | −9.1 |
| $10^2$/ml | — | — | 38.2 ± 10.6 | −2.0$^c$ | 37.7 ± 14.6 | −2.6$^c$ |
| $10^3$/ml | 19.3 ± 6.2 | 2.0$^c$ | 125.7 ± 80.5 | 85.4 | 67.4 ± 33.1 | 27.1 |
| $10^4$/ml | 48.4 ± 18.0 | 31.0$^d$ | 646.7 ± 196.5 | 606.4 | 364.0 ± 180.7 | 323.7 |
| $10^5$/ml | 365.9 ± 179.0 | 348.6 | 3370.2 ± 591.6 | 3329.9 | 1650.7 ± 670.4 | 1610.4 |
| $10^6$/ml | 2277.8 ± 658.7 | 2260.5 | 5464.8 ± 1086.3 | 5424.5 | 2923.2 ± 1178.9 | 2882.9 |
| $10^7$/ml | 2163.4 ± 642.0 | 2146.0 | 3318.3 ± 1509.2 | 3278.0 | 2498.6 ± 1338.3 | 2458.3 |

$^a$SALOD—Signal Above Limit of Detection
$^b$LOD—Baseline Limit of Detection value used to calculate sample SALOD values
$^c$Sporadically positive
$^d$Bold numbers indicate positive SALOD values Example 8

A new method for simultaneous detection and identification of pathogens is presented using a modified fluorescence in situ hybridization technique, which internally labels targeted nucleic acids, while still permitting antibody binding to surface antigens. This dual level specificity permits two levels of accuracy in determining presence or absence of pathogens within a complex matrix. Comparison of LQ-FISH processing to standard PFA slide based FISH indicated that comparable fluorescent signal was obtained for both *E. coli* O157:H7 and *S. aureus* cells. This denotes that the fixation and hybridization processing steps of CAT-FISH work with both Gram positive and Gram negative bacteria. While the fluorescent intensity of the *Staphylococcus* cells tended to be more variable than those of *E. coli*, this is not unexpected as *staphylococci* are known for hybridization difficulties due to membrane permeability issues (Amann et al., 1990; Roller et al., 1994). Permeability issues are typically overcome by use of lytic enzyme treatments prior to hybridization (Roller et al., 1994; Hogardt et al., 2000; Peters et al., 2006), and the use of lytic enzymes was observed to improve signal intensity for *S. aureus* in our assays (not shown). While Kempf et al. demonstrated the utility of lytic treatments; they also indicated that permeabilization can lead to cell destruction during centrifugation (Kempf et al., 2000; Kempf et al., 2005). However, with careful modulation, this can be overcome, as demonstrated here, and improved signal can be generated for gram-positive targets. In this study, both specific and general lytic agents were used to demonstrate improved probe accessibility options dependent upon whether or not the specific target is known to the investigator. As a further potential modification, Hartmann et al. have demonstrated the utility of peptide nucleic acid probes (PNA FISH) for overcoming staphylococcal permeability problems.

Methacarn treatment of *E. coli* allowed better antibody binding than that observed for untreated cells and two log better binding than that of cells treated with PFA prior to hybridization. After hybridization treatments, the methacarn treated cells still out performed PFA treated cells, but a one log reduction in sensitivity was observed (as compared to non-hybridized methacarn treated cells). This is likely due to the inclusion of formamide in the hybridization solution. The similarity in sensitivity for PFA treated cells (pre vs. post hybridization) suggests that the surface antigens were already damaged sufficiently, such that no further reduction in antibody binding was observed after formamide addition. Although possible to reformulate the hybridization conditions to maintain stringency with the exclusion of formamide, this would deviate from standard practices, and was out of the scope of this study (Stahl and Amann, 1991). The lack of significant differences between treatments for the *S. aureus* cells is likely due to the cell membrane and permeability issues as discussed previously. The two log decrease in sensitivity for *S. aureus* as compared to *E. coli* is most likely due to poorer quality of the antibody, since a 10-fold more concentrated stock was necessary to achieve detection, even for the untreated control.

LQ-FISH and antibody binding conditions were evaluated separately, with antibody binding assessed using a standard ELISA kit that was not based on FISH signal. Once both conditions were optimized and detection confirmed individually, both detection types were combined (CAT-FISH) and samples examined for labeling coverage. Both *E. coli* and *S. aureus* were sufficiently labeled by probe and antibody for easy visual detection. Whereas *E. coli* cells were fairly uniform in coverage, there seemed to be an alternating pattern for *S. aureus*. *S. aureus* cells that had high 16S rRNA signal had low antibody signal and vice versa. This may be due in part to growth phase of the cells in regard to ribosomal content and protein expression or a limitation to the current protocol.

The potential for CAT-FISH utility was further demonstrated on a commercially available cytometric bead array biosensor. CAT-FISH treated cells were successfully captured by magnetic array beads (IMS-CAT-FISH), and detected via signals emitted from the fluorescent probe. The BioPlex 200 was selected due to its popularity and the versatility of cytometric bead arrays, overall, but it should be noted that this platform is not optimized for detection of the CAT-FISH signal. Specifically, the BioPlex 200 is pre-set and optimized for the detection of cells externally labeled using a phycoerythrin-tagged antibody, not internally labeled with Alexa Fluor 532. The fluorophore used was one that matched detector specifics as closely as possible but it was not possible to exactly match the optimum detection conditions, since the excitation and emission wavelengths of the reader are pre-set and could not be altered.

The aforementioned compatibility discrepancies not withstanding, similar detection limits were achieved with IMS-CAT-FISH as compared to the standard assay for *E. coli*

O157:H7 in PBS buffer, and similar detection limits for *S. aureus* were also observed. This suggests that methacarn fixation permits sufficient target capture from a fluid matrix using antibody-coupled beads, and LQ-FISH generated fluorescent signals were ample enough to result in minimal to no loss in sensitivity. Notably, preliminary experiments to compare bead binding to PFA treated cells were unsuccessful in producing any signal and were not pursued.

Inasmuch as there may be problems between how well a detection method works in a laboratory buffer sample versus a real-world sample, additional sample matrices were tested. We have previously shown that detection of *E. coli* O157:H7 in enriched spinach rinse samples is possible using the cytometric array system, albeit with some difficulties due to background signals likely associated with the antibody used (Leach et al., 2010). We found that CAT-FISH is successful in detecting *E. coli* O157:H7 when used in conjugation with established spinach testing methods (rinsing and enrichment). It is interesting to note that microscopic evaluation of samples indicated that non-specific signals in standard antibody assays are due to binding of debris to antibody-coupled beads, as opposed to non-target cells (FIG. 4B). Thus, in this instance it was possible to use a general probe for the CAT-FISH procedure (since it labels only cells) to successfully eliminate the background problem.

We also evaluated the utility of CAT-FISH for *S. aureus* detection in an appropriate complex matrix. As bloodstream infections are commonly caused by *S. aureus*, we mimicked established blood testing conditions by spiking sheep blood with *S. aureus* and culturing in standard blood-culture media. We have observed cross-reactivity of our antibody with other *Staphylococcus* species (data not shown), so we chose to demonstrate the dual-label utility of CAT-FISH via incorporation of both a specific antibody and a specific probe. Our results indicated that specific antibodies can be used in association with specific probes to detect *S. aureus* in blood cultures via CAT-FISH.

Modification to further improve detection includes mainly optimizations specific to individual instruments, such as alignment of probe/detector excitation/emission pairs (e.g., BioPlex detection presented herein). Additionally, alteration of types and/or number of oligonucleotide probes used during hybridization may also be applied, (e.g., dual labeled FISH probe (DOPE-FISH) (Stoecker et al., 2010); peptide nucleic acid probes (Hartmann et al., 2005; Almeida et al., 2010) or multiple probes targeting different rRNA regions (Amann et al., 1990)). CAT-FISH also has the potential for transition to kit and/or multi-well plate formats, which would significantly reduce the amount of time required for processing per sample. Furthermore, should additional confirmation be necessary, treatment of bacterial cells with methacarn does not preclude assessment by PCR methods, and auxiliary (or alternate) analysis is possible prior to hybridization steps (data not shown).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 7,771,941
U.S. Pat. No. 5,429,797
U.S. Pat. No. 5,439,667
Almeida, C., Azevedo, N., Fernandes, R., Keevil, C. and Vieira, M. 2010. Fluorescence in situ hybridization method using a peptide nucleic acid probe for identification of *salmonella* spp. in a broad spectrum of samples. *Appl. Environ. Microbiol.* 76, 4476-4485.
Amann, R., Fuchs, B. M. and Behrens, S. 2001. The identification of microorganisms by fluorescence in situ hybridisation. *Curr. Opin. Biotechnol.* 12, 231-236.
Amann, R., Krumholz, L. and Stahl, D. A. 1990. Fluorescent-oligonucleotide probing of whole cells for determinative, phylogenetic, and environmental studies in microbiology. *J. Bacteriol.* 172, 762-770.
Amann, R. I. 1995. Fluorescently labeled, rRNA-targeted oligonucleotide probes in the study of microbial ecology. *Mol. Ecol.* 4, 543-554.
Amann, R. I., Binder, B. J., Olson, R. J., Chisholm, S. W., Devereux, R. and Stahl, D. A. 1990. Combination of 16s rRNA-targeted oligonucleotide probes with flow cytometry for analyzing mixed microbial populations. *Appl. Environ. Microbiol.* 56, 1919-1925.
Aβmus, B., Schloter, M., Kirchhof, G., Hutzler, P. and Hartmann, A. 1997. Improved in situ tracking of rhizosphere bacteria using dual staining with fluorescence-labeled antibodies and rRNA-targeted oligonucleotides. *Microb. Ecol.* 33, 32-40.
Baumgärtner, W., Dettinger, H., Schmeer, N. and Hoffmeister, E. 1988. Evaluation of different fixatives and treatments for immunohistochemical demonstration of *coxiella burnetii* in paraffin-embedded tissues. *J. Clin. Microbiol.* 26, 2044-2047.
Bisha, B. and Brehm-Stecher, B. F. 2009. Flow-through imaging cytometry for characterization of *Salmonella* subpopulations in alfalfa sprouts, a complex food system. *Biotechnol. J.* 4, 880-887.
Bisha, B. and Brehm-Stecher, B. F. 2009. Simple adhesive-tape sampling of tomato surfaces combined with rapid fluorescence in situ hybridization for *Salmonella* detection. *Appl. Environ. Microbiol.* 75, 1450-1455.
Beltz et al. (1983) *Methods of Enzymology*, R. Wu, L. Grossman and K. Moldave (eds.) Academic Press, New York 100:266-285.
Cox, M. L., Schray, C. L., Luster, C. N., Stewart, Z. S., Korytko, P. J., Khan, K. N., Paulauskis, J. D. and Dunstan, R. W. 2006. Assessment of fixatives, fixation, and tissue processing on morphology and RNA integrity. *Exp. Mol. Pathol.* 80, 183-191.
Daims, H., Lucker, S. and Wagner, M. 2006. Daime, a novel image analysis program for microbial ecology and biofilm research. *Environ. Microbiol.* 8, 200-213.
Daims, H., Stoecker, K. and Wagner, M. 2005. Fluorescence in situ hybridization for the detection of prokaryotes. In: Molecular microbial ecology: Advanced methods. A. M. Osborn and C. J. Smith. Taylor & Francis, Inc. Abington, UK. pp. 213-239.
DeLong, E., Wickham, G. and Pace, N. 1989. Phylogenetic stains: Ribosomal RNA-based probes for the identification of single cells. *Science* 243, 1360-1363.
Dotti, I. P., S. P. Bonin, G. D. Basili, E. P. Nardon, A. M. D. Balani, S. M. D. Siracusano, F. M. D. Zanconati, S. M. D.

Palmisano, N. M. D. De Manzini, and G. M. D. Stanta. 2010. Effects of Formalin, Methacarn, and FineFIX Fixatives on RNA Preservation. Diagn. Mol. Pathol. 19:112-122.

Feng, P., Weagant, S G, Grant, M A 1998. Enumeration of *Escherichia coli* and the coliform bacteria. *In: Bacteriological Analytical Manual Online.* 8th ed. U.S. Food and Drug Administration. Silver Spring, Md. http://www.fda.gov/Food/ScienceResearch/LaboratoryMethods/BacteriologicalAnalyticalManualBAM/UCM070080

Fuchs, B. M., Wallner, G., Beisker, W., Schwippl, I., Ludwig, W. and Amann, R. 1998. Flow cytometric analysis of the in situ accessibility of *Escherichia coli* 16s rRNA for fluorescently labeled oligonucleotide probes. *Appl. Environ. Microbiol.* 64, 4973-4982.

Hartmann, H., Stender, H., Schäfer, A., Autenrieth, I. B. and Kempf, V. A. J. 2005. Rapid identification of *Staphylococcus aureus* in blood cultures by a combination of fluorescence in situ hybridization using peptide nucleic acid probes and flow cytometry. *J. Clin. Microbiol.* 43, 4855-4857.

Hogardt, M., Trebesius, K., Geiger, A., Hornet M., Rosenbecker, J. and Heesemann, J. 2000. Specific and rapid detection by fluorescent in situ hybridization of bacteria in clinical samples obtained from cystic fibrosis patients. *J. Clin. Microbiol.* 38, 818-825.

Keller, G. H., M. M. Manak (1987) *DNA Probes*, Stockton Press, New York, N.Y., pp. 169-170.

Kempf, V. A. J., Mändle, T., Schumacher, U., Schafer, A. and Autenrieth, I. B. 2005. Rapid detection and identification of pathogens in blood cultures by fluorescence in situ hybridization and flow cytometry. Int. *J. Med. Microbiol.* 295, 47-55.

Kempf, V. A. J., Trebesius, K. and Autenrieth, I. B. 2000. Fluorescent in situ hybridization allows rapid identification of microorganisms in blood cultures. *J. Clin. Microbiol.* 38, 830-838.

Kim, J. S., Anderson, G. P., Erickson, J. S., Golden, J. P., Nasir, M. and Ligler, F. S. 2009. Multiplexed detection of bacteria and toxins using a microflow cytometer. *Anal. Chem.* (Washington, D.C., U.S.) 81, 5426-5432.

Kim, J. S., Taitt, C. R., Ligler, F. S. and Anderson, G. P. 2010. Multiplexed magnetic microsphere immunoassays for detection of pathogens in foods. *Sens. Instrum. Food Qual. Saf.* 4, 73-81.

Kohler, G., C. Milstein (1975) "Continuous cultures of fused cells secreting antibody of predefined specificity" *Nature* 256(5517):495-497.

Leach, K. M., Stroot, J. M. and Lim, D. V. 2010. Same-day detection of *Escherichia coli* O157:H7 from spinach by using electrochemiluminescent and cytometric bead array biosensors. *Appl. Environ. Microbiol.* 76, 8044-8052.

Leong, A. S. 1994. Fixatives and fixation. In: Laboratory histopathology: A complete reference. Eds. A. E. Woods and R. C. Ellis. Churchill-Livingstone. Edinburgh.

Li, X., De Boer, S. and Ward, L. 1997. Improved microscopic identification of *Clavibacter inichiganensis* subsp. *Sepedonicus* cells by combining in situ hybridization with immunofluorescence. *Lett. Appl. Microbiol.* 24, 431-434.

Lim, D. V., Simpson, J. M., Kearns, E. A. and Kramer, M. F. 2005. Current and developing technologies for monitoring agents of bioterrorism and biowarfare. *Clin. Microbiol. Rev.* 18, 583-607.

Loy, A., Maixner, F., Wagner, M. and Horn, M. 2007. Probebase—an online resource for rRNA-targeted oligonucleotide probes: New features 2007. *Nucleic Acids Res.* 35 (Database): D800-D804.

Maniatis et al. 1982, Molecular Cloning: A Laboratory Manual, Cold Spring Harbor Laboratory, New York.

Oerther, D. B., de los Reyes III, F. L., Hernandez, M. and Raskin, L. 1999. Simultaneous oligonucleotide probe hybridization and immunostaining for in situ detection of *Gordona* species in activated sludge. *FEMS Microbiol. Ecol.* 29, 129-136.

Oerther, D. B., Pemthaler, J., Schramm, A., Amann, R. and Raskin, L. 2000. Monitoring precursor 16s rRNAs of *Acinetobacter* spp. in activated sludge wastewater treatment systems. *Appl. Environ. Microbiol.* 66, 2154-2165.

Peters, R. P., van Agtmael, M. A., Simoons-Smit, A. M., Danner, S. A., Vandenbroucke-Grauls, C. M. and Savelkoul, P. H. M. 2006. Rapid identification of pathogens in blood cultures with a modified fluorescence in situ hybridization assay. *J. Clin. Microbiol.* 44, 4186-4188.

Ramage, G., Patrick, S. and Houston, S. 1998. Combined fluorescent in situ hybridisation and immunolabelling of *Bacteroides fragilis. J. Immunol. Methods* 212, 139-147.

Roller, C., Wagner, M., Amann, R., Ludwig, W. and Schleifer, K.-H. 1994. In situ probing of gram-positive bacteria with high DNA g+c content using 23s rRNA-targeted oligonucleotides. *Microbiology* 140, 2849-2858.

Shibutani, M. and Uneyama, C. 2002. Methacarn: A fixation tool for multipurpose genetic analysis from paraffin-embedded tissues. *Methods Enzymol.* 356,114-125.

Shibutani, M., Uneyama, C., Miyazaki, K., Toyoda, K. and Hirose, M. 2000. Methacarn fixation: A novel tool for analysis of gene expressions in paraffin-embedded tissue specimens. *Lab. Invest.* 80, 199-208.

Simpson-Stroot, J. M., Kearns, E. A., Stroot, P. G., Magaña, S. and Lim, D. V. 2008. Monitoring biosensor capture efficiencies: Development of a model using GFP-expressing *Escherichia coli* O157:H7. *J. Microbiol. Methods* 72, 29-37.

Srinivasan, M., Sedmak, D. and Jewell, S. 2002. Effect of fixatives and tissue processing on the content and integrity of nucleic acids. *Am. J. Pathol.* 161, 1961-1971.

Stahl, D. A. and Amann, R. 1991. Development and application of nucleic acid probes. In: Nucleic acid techniques in bacterial systematics. E. Stackebrandt and M. Goodfellow. John Wiley and Sons, Ltd. New York. pp. 205-248.

Stoecker, K., Dorninger, C., Daims, H. and Wagner, M. 2010. Double labeling of oligonucleotide probes for fluorescence in situ hybridization (DOPE-FISH) improves signal intensity and increases rRNA accessibility. *Appl. Environ. Microbiol.* 76, 922-926.

Suggs et al. (1981) *ICN-UCLA Symp. Dev. Biol. Using Purified Genes*, D. D. Brown (ed.), Academic Press, New York, 23:683-693.

Urieli-Shoval, S., R. L. Meek, R. H. Hanson, M. Ferguson, D. Gordon, and E. P. Benditt. 1992. Preservation of RNA for in situ hybridization: Carnoy's versus formaldehyde fixation. J. Histochem. Cytochem. 40:1879-1885.

Wagner, M., Horn, M. and Daims, H. 2003. Fluorescence in situ hybridisation for the identification and characterisation of prokaryotes. *Curr. Opin. Microbiol.* 6, 302-309.

Wallner, G., Amann, R. and Beisker, W. 1993. Optimizing fluorescent in situ hybridization with rRNA-targeted oligonucleotide probes for flow cytometric identification of microorganisms. *Cytometry* 14, 136-143.

Wallner, G., Fuchs, B., Spring, S., Beisker, W. and Amann, R. 1997. Flow sorting of microorganisms for molecular analysis. *Appl. Environ. Microbiol.* 63, 4223-4231.

Wellinghausen, N., Nockler, K., Sigge, A., Bartel, M., Essig, A. and Poppert, S. 2006. Rapid detection of *Brucella* spp.

in blood cultures by fluorescence in situ hybridization. *J. Clin. Microbiol.* 44, 1828-1830.

Yang, T. T. et al. (1996) "Optimized Codon Usage and Chromophore Mutations Provide Enhanced Sensitivity with the Green Fluorescent Protein" *Nucleic Acid Research* 24(22):4592-4593.

We claim:

1. A method for detecting a target bacterial cell in a population of cells, wherein the method comprises:
   a) obtaining a sample of cells from the population of cells;
   b) fixing the cells in a methacarn solution that will allow for antibody binding to one or more antigens on the surface of the cells after hybridization processing steps, wherein the methacarn solution comprises chloroform and wherein the cells are fixed in the methacarn solution for about 10 minutes;
   c) dehydrating the fixed cells;
   d) contacting the fixed cells with a fluorescently labeled oligonucleotide probe that hybridizes specifically with ribosomal RNA (rRNA) of the target bacterial cell under suitable hybridization conditions;
   e) contacting the cells after step d) with antibody immobilized on the surface of a bead, wherein the antibody binds to one or more antigens on the surface of the target bacterial cell and isolating the beads having target bacterial cells bound to the surface of the bead; and
   f) detecting the fluorescently labeled oligonucleotide probe hybridized to rRNA of the target bacterial cell to thereby detect the target bacterial cell.

2. The method according to claim 1, wherein the antibody is a monoclonal antibody.

3. The method according to claim 1, wherein the antibody is a polyclonal antibody.

4. The method according to claim 2, wherein the antibody is an antigen binding fragment selected from Fab, Fab', (Fab')$_2$, or Fv fragment, or is a single chain antibody.

5. The method according to claim 3, wherein the antibody is an antigen binding fragment selected from Fab, Fab', (Fab')$_2$, or Fv fragment, or is a single chain antibody.

6. The method according to claim 1, wherein the methacarn solution comprises 6 parts absolute methanol, 3 parts chloroform, and 1 part glacial acetic acid.

7. The method according to claim 1, wherein the oligonucleotide probe comprises the nucleotide sequence shown in SEQ ID NO:1 or SEQ ID NO:2.

8. The method according to claim 1, wherein the cell sample is obtained from water, soil, slurry, sludge, gas, liquid, or vapor.

9. The method according to claim 1, wherein step a) further comprises isolating cells from the sample.

10. The method according to claim 9, wherein the cells are isolated by centrifugation of the sample in step a).

11. The method according to claim 1, wherein the cells are dehydrated in step c) using one or more ethanol washes and/or air drying.

12. The method according to claim 1, wherein the detectably labeled oligonucleotide probe is labeled with a fluorescent label, a chemiluminescent reagent, a bioluminescent reagent, an enzyme, or a radioisotope.

13. The method according to claim 1, wherein after step d) the cells are centrifuged and resuspended in a suitable buffer one or more times.

14. The method according to claim 1, wherein the bead can be attracted by a magnetic field and the bead having target cells bound thereto is isolated by applying a magnetic field.

15. The method according to claim 14, wherein the bead is a magnetic or super paramagnetic bead.

16. The method according to claim 1, wherein the bound target bacterial cells are washed one or more times prior to detecting the detectably labeled oligonucleotide probe.

17. The method according to claim 1, wherein the rRNA is 16S and/or 23S RNA.

18. The method according to claim 1, wherein the bacterial cell is *Nitrospira* spp., *Nitrosospira* spp., *Nitrobacter* spp., *Nitrosomonas* spp., *Clostridium* spp., *Bacillus* spp., methanogenic archaea, coliforms, *Salmonella* spp., *Bacteroides* spp., *Staphylococcus* spp., *Streptococcus* spp., *Neis-* seria spp., *Haemophilus* spp., *Bordetella* spp., *Listeria* spp., *Mycobacterium* spp., *Shigella* spp., *Pseudomonas* spp., *Brucella* spp., *Treponema* spp., *Mycoplasma* spp., *Yersinia* spp., *Vibrionaceae* spp., *Chlamydia* spp., *Legionella* spp., *Escherichia* spp., *Acinetobacter* spp., *Burkholderia* spp., *Thiobacillus* spp., *Rickettsia* spp., *Sphinomonas* spp., *Francisella* spp., *Campylobacter* spp., or *Helicobacter* spp.

19. The method according to claim 1, wherein the hybridization conditions in step d) are stringent hybridization conditions.

20. The method according to claim 1, wherein the bead is a microbead.

21. The method according to claim 1, wherein the bead contains a detectable label or fluorophore.

22. The method according to claim 1, wherein after step b) the fixed cells are contacted with one or more lytic enzymes.

23. The method according to claim 22, wherein the lytic enzyme is lysozyme.

24. The method according to claim 1, wherein the bacterial cell is *E. coli*.

25. The method according to claim 22, wherein the lytic enzyme is lysostaphin.

26. The method according to claim 22, wherein the lytic enzyme is nisin.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial sequence
<220> FEATURE:
<223> OTHER INFORMATION: an oligonucleotide hybridization probe
      targeting the 16S rRNA for the domain Eubacteria

<400> SEQUENCE: 1
gctgcctccc gtaggagt                                                   18

<210> SEQ ID NO 2
<211> LENGTH: 19
<212> TYPE: DNA
<213> ORGANISM: Artificial sequence
<220> FEATURE:
<223> OTHER INFORMATION: an oligonucleotide hybridization probe
      targeting the 16S rRNA for the species S. aureus

<400> SEQUENCE: 2
gaagcaagct tctcgtccg                                                  19
```

UNITED STATES PATENT AND TRADEMARK OFFICE
CERTIFICATE OF CORRECTION

PATENT NO. : 9,714,943 B2
APPLICATION NO. : 13/336800
DATED : July 25, 2017
INVENTOR(S) : Joyce Marie Stroot et al.

It is certified that error appears in the above-identified patent and that said Letters Patent is hereby corrected as shown below:

In the Specification

Column 12,
Line 61, "(Cd-Line)" should read --(Cel-Line)--.

Column 21,
Line 22, "Hornet M" should read --Hornef, M--.
Line 29, "Schafer, A" should read --Schäfer, A--.
Line 57, "*inichiganensis*" should read --*michiganensis*--.

Signed and Sealed this
Twenty-eighth Day of August, 2018

Andrei Iancu
*Director of the United States Patent and Trademark Office*